US008966694B2

(12) United States Patent
Iwahori et al.

(10) Patent No.: US 8,966,694 B2
(45) Date of Patent: Mar. 3, 2015

(54) ELECTRIC TOOTHBRUSH

(75) Inventors: Toshiyuki Iwahori, Mishima-gun (JP); Jun Shimoyama, Uji (JP); Kuniyoshi Takahashi, Kusatsu (JP); Hiroshi Yoshida, Hirakata (JP)

(73) Assignee: Omron Healthcare Co., Ltd., Kyoto-Shi (JP)

(*) Notice: Subject to any disclaimer, the term of this patent is extended or adjusted under 35 U.S.C. 154(b) by 690 days.

(21) Appl. No.: 12/990,368

(22) PCT Filed: Apr. 28, 2009

(86) PCT No.: PCT/JP2009/058401
§ 371 (c)(1), (2), (4) Date: Oct. 29, 2010

(87) PCT Pub. No.: WO2009/136579
PCT Pub. Date: Nov. 12, 2009

(65) Prior Publication Data

US 2011/0056033 A1 Mar. 10, 2011

(30) Foreign Application Priority Data

May 9, 2008 (JP) ................................ 2008-123929

(51) Int. Cl.
*A61C 17/22* (2006.01)
*A61C 17/34* (2006.01)
(Continued)

(52) U.S. Cl.
CPC ............... *A61C 17/3481* (2013.01); *A46B 5/02* (2013.01); *A46B 15/0006* (2013.01); *A61C 17/225* (2013.01); *A46B 2200/1066* (2013.01)
USPC ............................................ 15/22.1; 15/105

(58) Field of Classification Search
USPC ..................... 15/22.1, 28, 105, 22.2; D4/107
See application file for complete search history.

(56) References Cited

U.S. PATENT DOCUMENTS 4,149,291 A 4/1979 Stoltz
6,230,717 B1 * 5/2001 Marx et al. .................... 132/308
(Continued)

FOREIGN PATENT DOCUMENTS

GB 2252234 A * 8/1992 ............ A46B 15/00
JP U-62-185533 11/1987
(Continued)

OTHER PUBLICATIONS

International Search Report dated May 26, 2009 in corresponding International Application No. PCT/JP2009/058401 (with translation).

(Continued)

*Primary Examiner* — Gary Graham
*Assistant Examiner* — Michael Jennings
(74) *Attorney, Agent, or Firm* — Oliff PLC

(57) ABSTRACT

There is provided an electric toothbrush with which teeth can be brushed in a relaxed pose while imperfect brushing is suppressed.

In an electric toothbrush including: a body portion that is gripped by a hand during toothbrushing; and a brush component serving as an intraoral insertion portion inserted in a mouth cavity during the toothbrushing, the brush component including a brush at a leading end thereof, the brush component is inclined onto a rear surface side of the brush from the leading end toward the body portion, and a leading end portion of the brush component is located in a vicinity of an extended line (alternate long and short dash line) of a virtual line that connects centroids of sectional shapes perpendicular to a longitudinal direction in the body portion.

5 Claims, 17 Drawing Sheets

(51) Int. Cl.
*A46B 5/02* (2006.01)
*A46B 15/00* (2006.01)

(56) References Cited

U.S. PATENT DOCUMENTS

| | | | | | |
|---|---|---|---|---|---|
| D494,371 | S | * | 8/2004 | Berde | D4/105 |
| D495,142 | S | * | 8/2004 | Berde | D4/105 |
| 6,932,216 | B2 | * | 8/2005 | Blaustein et al. | 206/362.2 |
| 7,020,925 | B1 | * | 4/2006 | Gitelis | 15/22.1 |
| 7,240,390 | B2 | * | 7/2007 | Pfenniger et al. | 15/22.1 |
| 7,596,827 | B1 | * | 10/2009 | Puneet | 15/22.1 |
| 7,600,284 | B2 | * | 10/2009 | Hui et al. | 15/22.1 |
| 7,713,461 | B2 | * | 5/2010 | Pfenniger et al. | 264/272.21 |
| 7,721,371 | B2 | * | 5/2010 | Pfenniger et al. | 15/22.1 |
| 7,774,886 | B2 | * | 8/2010 | Hilscher et al. | 15/22.1 |
| 7,784,138 | B2 | * | 8/2010 | Spooner | 15/22.2 |
| 7,845,039 | B2 | * | 12/2010 | Chan et al. | 15/22.1 |
| 7,861,349 | B2 | * | 1/2011 | Hilscher et al. | 15/22.1 |
| 7,917,986 | B2 | * | 4/2011 | Jimenez et al. | 15/167.1 |
| 8,011,057 | B2 | * | 9/2011 | Nejat | 15/167.1 |
| 8,239,995 | B2 | * | 8/2012 | Chenvainu et al. | 15/167.1 |
| 8,365,335 | B2 | * | 2/2013 | Fischer et al. | 15/22.1 |
| 2002/0039720 | A1 | * | 4/2002 | Marx et al. | 433/216 |
| 2003/0182745 | A1 | * | 10/2003 | Hartman et al. | 15/22.1 |
| 2003/0194678 | A1 | * | 10/2003 | Viltro et al. | 433/80 |
| 2004/0016069 | A1 | * | 1/2004 | Lee | 15/28 |
| 2004/0088807 | A1 | * | 5/2004 | Blaustein et al. | 15/22.1 |
| 2005/0102774 | A1 | * | 5/2005 | Drossler | 15/22.1 |
| 2005/0150067 | A1 | * | 7/2005 | Cobabe et al. | 15/22.1 |
| 2006/0048315 | A1 | * | 3/2006 | Chan et al. | 15/22.1 |
| 2006/0150350 | A1 | * | 7/2006 | Pfenniger et al. | 15/22.1 |
| 2007/0294847 | A1 | * | 12/2007 | Wang | 15/22.2 |
| 2008/0006549 | A1 | * | 1/2008 | Chan | 206/361 |
| 2008/0196184 | A1 | * | 8/2008 | Mary T. | 15/22.1 |
| 2009/0019649 | A1 | * | 1/2009 | Dickie | 15/22.1 |
| 2009/0064430 | A1 | * | 3/2009 | Jimenez et al. | 15/22.1 |

FOREIGN PATENT DOCUMENTS

| | | | | |
|---|---|---|---|---|
| JP | 02-28744 | | | 8/1990 |
| JP | Y2-2-28744 | | | 8/1990 |
| JP | A-5-115321 | | | 5/1993 |
| JP | A-10-192054 | | | 7/1998 |
| JP | 2001-128995 | | | 5/2001 |
| JP | A-2001-128995 | | | 5/2001 |
| JP | A-2007-503269 | | | 2/2007 |
| JP | 2007-325806 | | | 12/2007 |
| JP | A-2007-325806 | | | 12/2007 |
| JP | 2008-080099 | | | 4/2008 |
| JP | A-2008-80099 | | | 4/2008 |
| JP | U-3140630 | | | 4/2008 |
| WO | WO 02/054906 | A1 | | 7/2002 |
| WO | WO 2005/023145 | A2 | | 3/2005 |
| WO | WO 2005067764 | A1 | * | 7/2005 |
| WO | WO 2005/070324 | A2 | | 8/2005 |
| WO | WO 2006/119205 | A2 | | 11/2006 |
| WO | WO 2008/076383 | A1 | | 3/2008 |

OTHER PUBLICATIONS

Jan. 19, 2012 Russian Office Action issued in Russian Patent Application No. 2010150476 (with translation).

Office Action issued in Chinese Patent Application No. 200980116252.8 dated Jul. 5, 2012 (with translation).

Mar. 19, 2013 Office Action issued in Japanese Patent Application No. 2008-123929 (with translation).

* cited by examiner

ELECTRIC TOOTHBRUSH

TECHNICAL FIELD

The present invention relates to an electric toothbrush.

BACKGROUND ART

Conventionally, there is well known an electrically driven electric toothbrush (see Patent Documents 1 and 2). Generally, because various components such as a driving source are incorporated in the electric toothbrush, the electric toothbrush is enlarged in comparison with an ordinary toothbrush. More specifically, the electric toothbrush is configured such that a portion gripped by a hand is lengthened and thickened in comparison with the ordinary toothbrush. Thus, a distance from the portion gripped by the hand to a vicinity of a mouth is lengthened in comparison with the ordinary toothbrush. Accordingly, when toothbrushing is performed with use of the electric toothbrush, a motion area of an arm is generally widened while brushing entirely the teeth in comparison with the toothbrushing with the ordinary toothbrush. In comparison with the ordinary toothbrush, it is necessary to firmly grip a body portion of the electric toothbrush during the toothbrushing.

Because the electric toothbrush is enlarged in comparison with the ordinary toothbrush, upon brushing a back tooth, particularly in a case where a surface on a cheek side of the back tooth is brushed, it is necessary that the body portion be firmly gripped to brush the tooth while an elbow is highly raised, and the user tends to take an unusual pose. Moreover, imperfect brushing is easily caused due to this inconvenience. Particularly, when the brush abuts on the back tooth, a leading end surface of the brush and a plane in which the teeth are aligned are deviated from each other while being not parallel to each other, and there is sometimes a point on which the brush does not actually properly abut to cause imperfect brushing although a user has a sense of the brush abutting properly on the entire back tooth.

PRIOR ART DOCUMENTS

Patent Documents

Patent Document 1: Japanese Unexamined Patent Publication No. H10-192054

Patent Document 2: Japanese Published Patent Publication No. 2007-503269

SUMMARY OF THE INVENTION

Problem to be Solved by the Invention

An object of the present invention is to provide an electric toothbrush with which teeth can be brushed in a relaxed pose while imperfect brushing is suppressed.

Means for Solving Problem

In the present invention, the following means are adopted in order to solve the above problem.

An electric toothbrush according to the present invention includes: a body portion that is gripped by a hand during toothbrushing; and an intraoral insertion portion that is inserted in a mouth cavity during the toothbrushing, the intraoral insertion portion including a brush at a leading end thereof, wherein the intraoral insertion portion is inclined onto a rear surface side of the brush from the leading end toward the body portion, and a leading end portion of the intraoral insertion portion is located in a vicinity of an extended line of a virtual line that connects centroids of sectional shapes perpendicular to a longitudinal direction in the body portion.

According to the electric toothbrush of the present invention, the intraoral insertion portion that is inserted in the mouth cavity during the toothbrushing is inclined on the rear surface side of the brush from the leading end toward the body portion, and the leading end portion of the intraoral insertion portion is located in the vicinity of the extended line of the virtual line that connects the centroids of the sectional shapes perpendicular to the longitudinal direction in the body portion. Therefore, a motion area of an arm is narrowed while brushing a back tooth where imperfect brushing is easily caused, in comparison with a general electric toothbrush configured such that a body portion and an intraoral insertion portion are aligned straight. That is, with the electric toothbrush of the present invention, a moving area of the body portion is concentrated on the vicinity in front of the mouth when the back tooth is brushed. Therefore, the motion area of the arm is narrowed with no need for highly raising an elbow. Accordingly, the toothbrushing can be performed in a relaxed pose. When the brush abuts on the back tooth, the brush can abut properly on the entire back tooth in a relaxed pose. Therefore, imperfect brushing can be suppressed.

There may be provided a connection portion that is inclined onto the rear surface side of the brush from the leading end of the body portion toward the brush, the connection portion connecting the body portion and the intraoral insertion portion.

There may be provided: an eccentric shaft that is provided in the intraoral insertion portion; and a motor that rotates the eccentric shaft.

In this configuration, the motor rotates the eccentric shaft, which generates vibration to vibrate the brush.

The motor may be provided in the connection portion.

In this configuration, bent (curved) points from the rotating shaft of the motor to the eccentric shaft can be reduced to suppress degradation of the transmission efficiency of the driving force.

A rotating shaft of the motor and the eccentric shaft may be coupled to each other by a rod having flexibility.

In this configuration, the length of the rod having flexibility can be shortened to enhance the transmission efficiency of the driving force.

It is also preferable that the eccentric shaft itself has flexibility.

In this configuration, the driving force can be transmitted with a small number of components.

A display portion in which display information is changed may be provided in an area including at least part of a surface on the brush side of the connection portion.

In this configuration, the display portion can be visibly recognized even during the toothbrushing.

A manipulation portion that includes a plurality of buttons to manipulate motions of the electric toothbrush may be provided in an area from the body portion to the connection portion, and The buttons to perform different manipulations may be disposed separately in the body portion and the connection portion.

In this configuration, the user can easily distinguish the buttons to be manipulated. For example, the button used to power on the electric toothbrush is disposed on the connection portion side, and the button used to power off the electric toothbrush is disposed on the body portion side, which allows the manipulation to be simply performed when the electric toothbrush is powered on or off.

The above-described configurations are adopted in combination as much as possible.

Effect of the Invention

As described above, according to the present invention, during the toothbrushing, the tooth can be brushed in a relaxed pose, and imperfect brushing can be suppressed.

MODES FOR CARRYING OUT THE INVENTION

On the basis of the embodiments, modes for carrying out the present invention will be described exemplarily in detail below with reference to the drawings. However, the scope of the present invention is not limited to sizes, materials, and shapes of components described in the following embodiments as well as relative dispositions thereof unless otherwise noted.

(First Embodiment)

An electric toothbrush according to a first embodiment of the present invention will be described with reference to FIGS. 1 to 15.

<Appearance Configuration of Electric Toothbrush>

Figure 1:
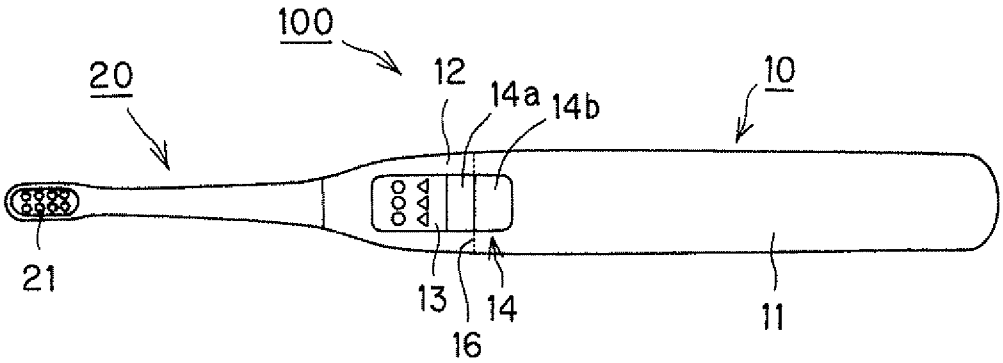
FIG. 1 is a front view of an electric toothbrush according to a first embodiment of the present invention.
Figure 2:
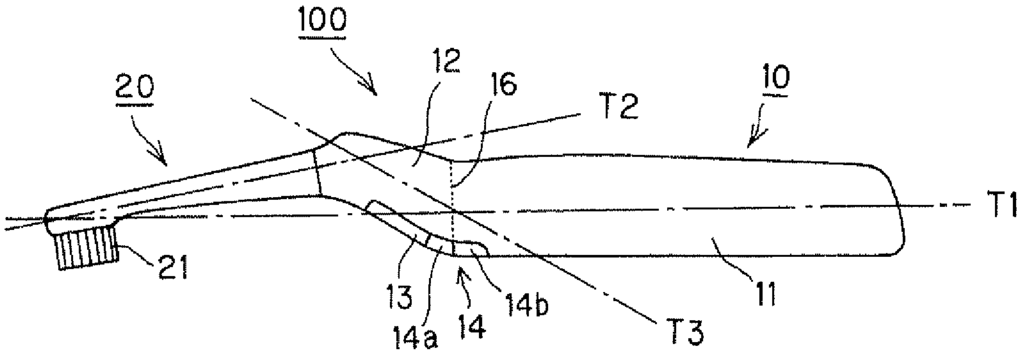
FIG. 2 is a side view of the electric toothbrush according to the first embodiment of the present invention.
Figure 3:
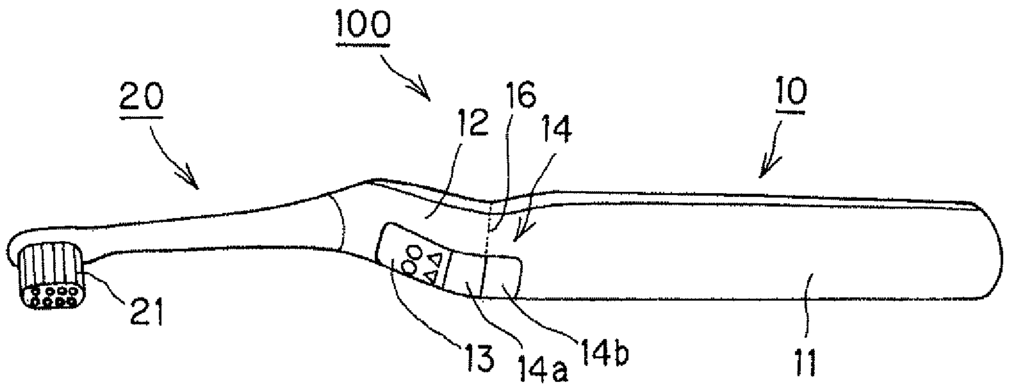
FIG. 3 is a perspective view of the electric toothbrush according to the first embodiment of the present invention when viewed from a front side.
Figure 4:
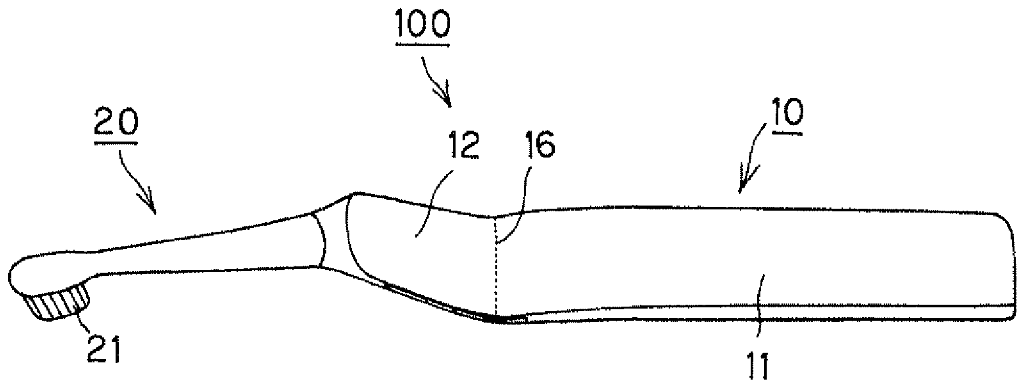
FIG. 4 is a perspective view of the electric toothbrush according to the first embodiment of the present invention when viewed from a rear side.

An appearance configuration of the electric toothbrush according to the first embodiment of the present invention will be described with reference to FIGS. 1 to 4. FIG. 1 is a front view of the electric toothbrush according to the first embodiment of the present invention. FIG. 2 is a side view of the electric toothbrush according to the first embodiment of the present invention. FIG. 3 is a perspective view of the electric toothbrush according to the first embodiment of the present invention when viewed from a front side. FIG. 4 is a perspective view of the electric toothbrush according to the first embodiment of the present invention when viewed from a rear side.

An electric toothbrush 100 according to the present embodiment includes a case 10 and a brush component 20. The case 10 includes a driving source therein, and the brush component 20 is detachably attached to the case 10.

The brush component 20 is a portion that is inserted in a mouth cavity during toothbrushing, and corresponds to an intraoral insertion portion. A brush 21 is provided at a leading end of the brush component 20.

The case 10 includes a substantially cylindrical portion and a bent portion that is provided while being bent from a leading end portion 16 of the substantially cylindrical portion. The substantially cylindrical portion of the case 10 is gripped by a hand during the toothbrushing. Hereinafter, the substantially cylindrical portion to be gripped by the hand during the toothbrushing is referred to as a body portion 11. The bent portion of the case 10 connects the body portion 11 and the brush component 20 serving as the intraoral insertion portion. Hereinafter, the bent portion is referred to as a connection portion 12.

A display portion 13 is provided in an area including part of a surface on the side of the brush 21 of the connection portion 12. Information displayed on the display portion 13 can be changed during charging, in each time of toothbrushing, or during toothbrushing. Examples of the displayed information include a selection mode in a case where a plurality of driving modes (in the present embodiment, vibration modes as described later) of the brush 21 can be selected, a remaining battery level, an elapsed period of time of the toothbrushing, and a state of realizing an optimum brush angle.

In the present embodiment, a manipulation portion 14 is provided adjacent to the display portion 13. The manipulation portion 14 includes a switch to power on and off and a button group to perform various settings including changes of various modes. In the present embodiment, an on-switch button **14*a* to power on and an off-switch button 14*b* to power off are provided in the manipulation portion 14. The on-switch button 14*a* is provided in a surface on the side of the brush 21 of the connection portion 12. The off-switch button 14*b* is provided in a surface on the side of the brush 21 of the body portion 11**.

In the electric toothbrush 100 according to the present embodiment, as described above, the body portion 11 is formed into the substantially cylindrical shape, and a virtual line connecting centroids of sectional shapes perpendicular to a longitudinal direction in the body portion 11 forms a substantially straight line. In FIG. 2, an alternate long and short dash line T1 includes the virtual line and an extended line of the virtual line. The connection portion 12 is also formed into a substantially cylindrical shape, and a virtual line connecting centroids of sectional shapes perpendicular to a longitudinal direction in the connection portion 12 also forms a substantially straight line. In FIG. 2, an alternate long and short dash line T3 includes the virtual line and an extended line of the virtual line.

In the brush component 20 serving as the intraoral insertion portion, a portion except the brush 21 is formed into a substantially circular truncated cone shape. A virtual line connecting centroids of sectional shapes perpendicular to a longitudinal direction in this portion also forms a substantially straight line. In FIG. 2, an alternate long and short dash line T2 includes the virtual line and an extended line of the virtual line.

As can be seen from a relationship among the alternate long and short dash lines T1, T2, and T3, the brush component 20 is inclined onto a rear surface side of the brush 21 from the leading end toward the body portion 11. In the present embodiment, the brush component 20 is configured such that a back end thereof is extended to a position projected toward the rear surface from the body portion 11. The leading end portion of the brush component 20 is located in the vicinity of the extended line (alternate long and short dash line T1) of the virtual line that connects the centroids of the sectional shapes perpendicular to the longitudinal direction in the body portion 11.

The connection portion 12 is inclined to the rear surface side of the brush 21 toward the brush 21 from the leading end of the body portion 11.

<Internal Configuration of Electric Toothbrush>

Figure 5:
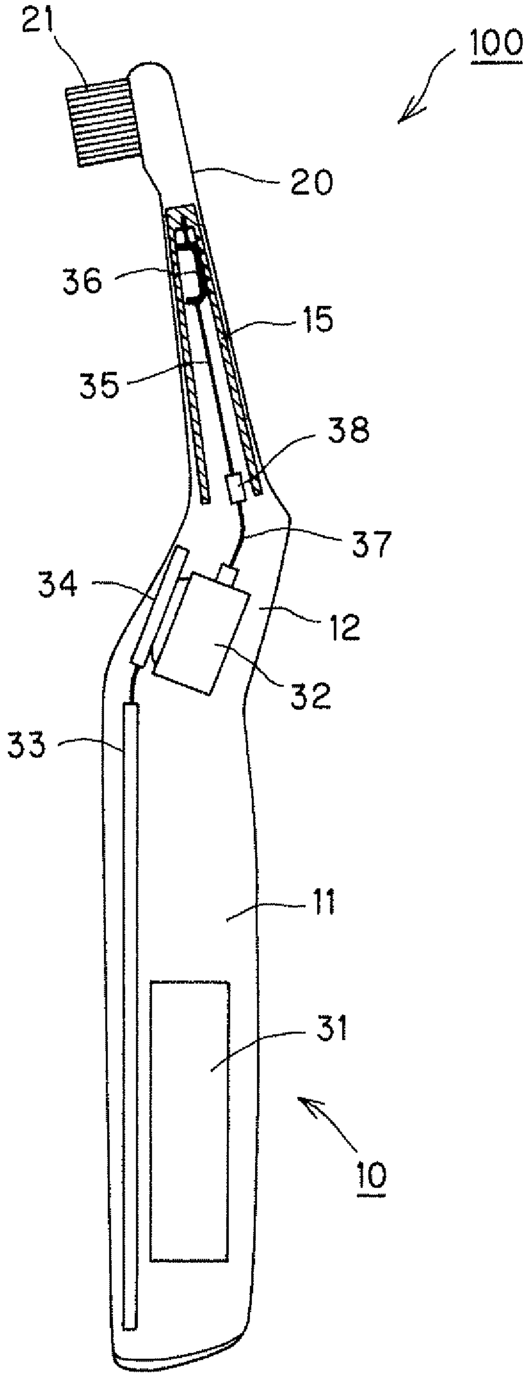
FIG. 5 is a schematic diagram (perspective view) illustrating a main configuration of an inside of the electric toothbrush according to the first embodiment of the present invention.

An internal configuration of the electric toothbrush according to the first embodiment of the present invention will be described with reference to FIG. 5. FIG. 5 is a schematic diagram (perspective view) illustrating a main configuration of an inside of the electric toothbrush according to the first embodiment of the present invention.

A battery (rechargeable battery) 31, a motor 32 serving as a driving source, and circuit boards 33 and 34 that include various electronic components and interconnections are accommodated in the case 10. The battery 31 is provided in the body portion 11, and the motor 32 is provided in the connection portion 12.

A stem 15 is provided on the leading end side of the case 10. One end of the stem 15 is supported by the inside of the case 10, and the other end is projected from an opening in the leading end of the case 10. The brush component 20 is mounted such that the stem 15 is covered therewith.

An eccentric shaft 35 including a weight 36 is provided on the leading end side of the case 10, and a gravity center of the weight 36 is deviated from an axis center. The eccentric shaft 35 is provided in the stem 15, that is, in the brush component 20 serving as the intraoral insertion portion. The weight 36 included in the eccentric shaft 35 is provided so as to be located in the vicinity of the brush 21.

A rotating shaft of the motor 32 and the eccentric shaft 35 are coupled to each other by a rod having flexibility (hereinafter, referred to as a flexible rod 37). The flexible rod 37 and the eccentric shaft 35 are connected to each other by a connection terminal 38. An end portion on the side of the weight 36 of the eccentric shaft 35 is supported by a bearing that is provided at the leading end of the stem 15.

Motions of the electric toothbrush 100 having the above-described configuration will be described. When the electric toothbrush 100 is powered on by the switch provided in the manipulation portion 14, the rotating shaft of the motor 32 is rotated, and the eccentric shaft 35 is rotated via the flexible rod 37 that is fixed to the rotating shaft. As described above, the weight 36 is provided in the eccentric shaft 35 while the gravity center of the weight 36 is deviated from the axis center. Therefore, if the eccentric shaft 35 is rotated while the leading end of the eccentric shaft 35 is not supported by the bearing, the eccentric shaft 35 gyrates around the axis center while being rotated. Therefore, when the eccentric shaft 35 is rotated while being supported by the bearing at the leading end of the stem 15, an outer wall surface in the vicinity of the leading end of the eccentric shaft 35 can be operated such as to repeatedly collide with an inner wall surface of the bearing many times in a short period of time.

The stem 15 can be vibrated by performing this operation. The vibration of the stem 15 can be transmitted to the brush component 20 fixed to the stem 15. Accordingly, because the brush 21 is vibrated by the vibration of the brush component 20, the brush 21 can abut on the teeth to perform the toothbrushing.

<Advantage of First Embodiment>

As described above, in the electric toothbrush 100 according to the present embodiment, the brush component 20 serving as the intraoral insertion portion inserted in the mouth cavity during the toothbrushing is inclined onto the rear surface side of the brush 21 from the leading end toward the body portion 11, and the leading end portion of the brush component 20 is located in the vicinity of the extended line (alternate long and short dash line T1) of the virtual line connecting the centroids of the sectional shapes perpendicular to the longitudinal direction in the body portion 11.

According to the electric toothbrush 100 of the present embodiment, in comparison with a general electric toothbrush configured such that the body portion and the intraoral insertion portion are aligned straight, the teeth can be brushed in a relaxed pose, and imperfect brushing can be suppressed. This feature will be described in detail with reference to FIGS. 6 to 15.

Figure 6:
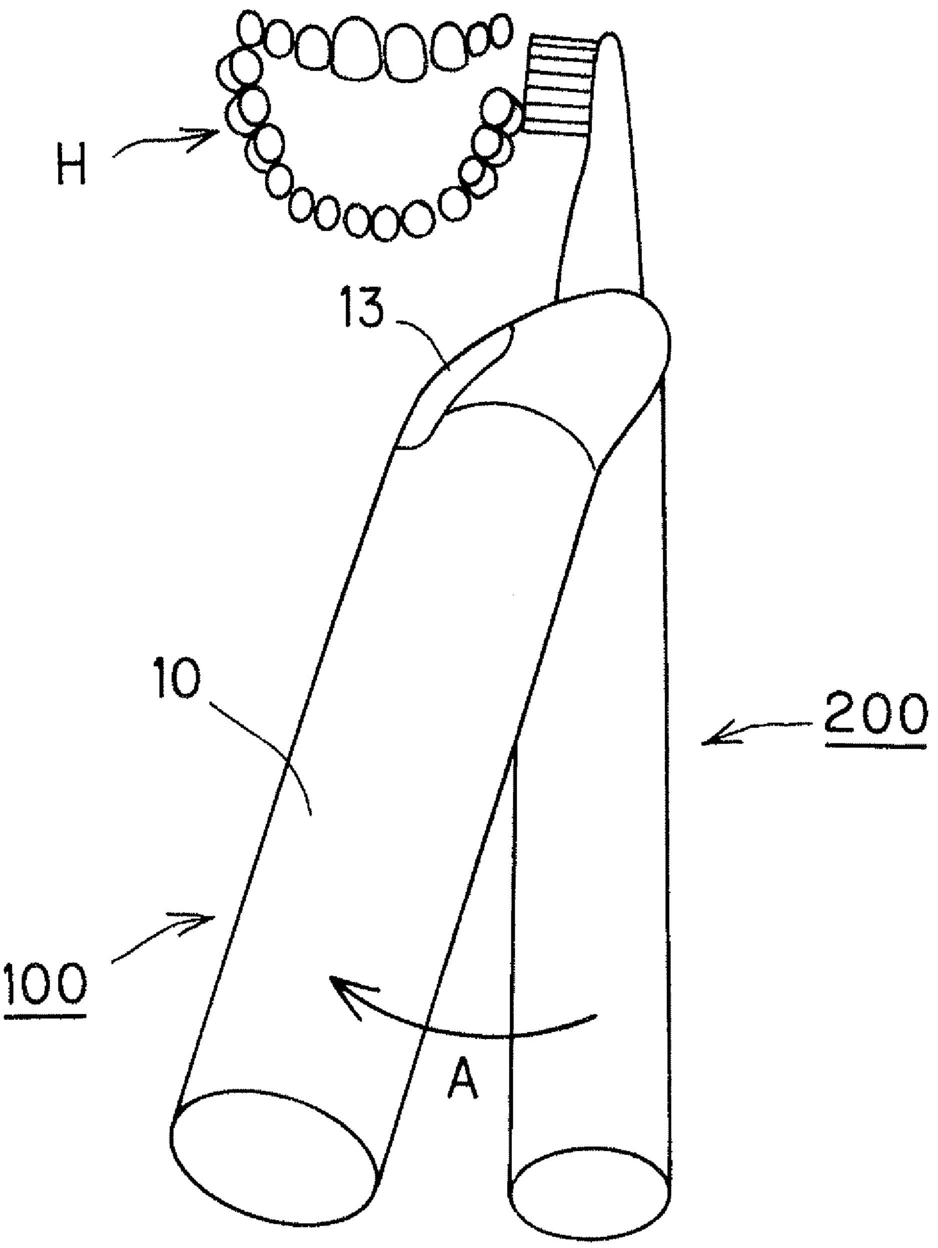
FIG. 6 is a view in which positions of the electric toothbrush according to the first embodiment of the present invention and an electric toothbrush according to a comparative example are compared to each other when a brush surface abuts (properly) on a left back tooth.
Figure 7:
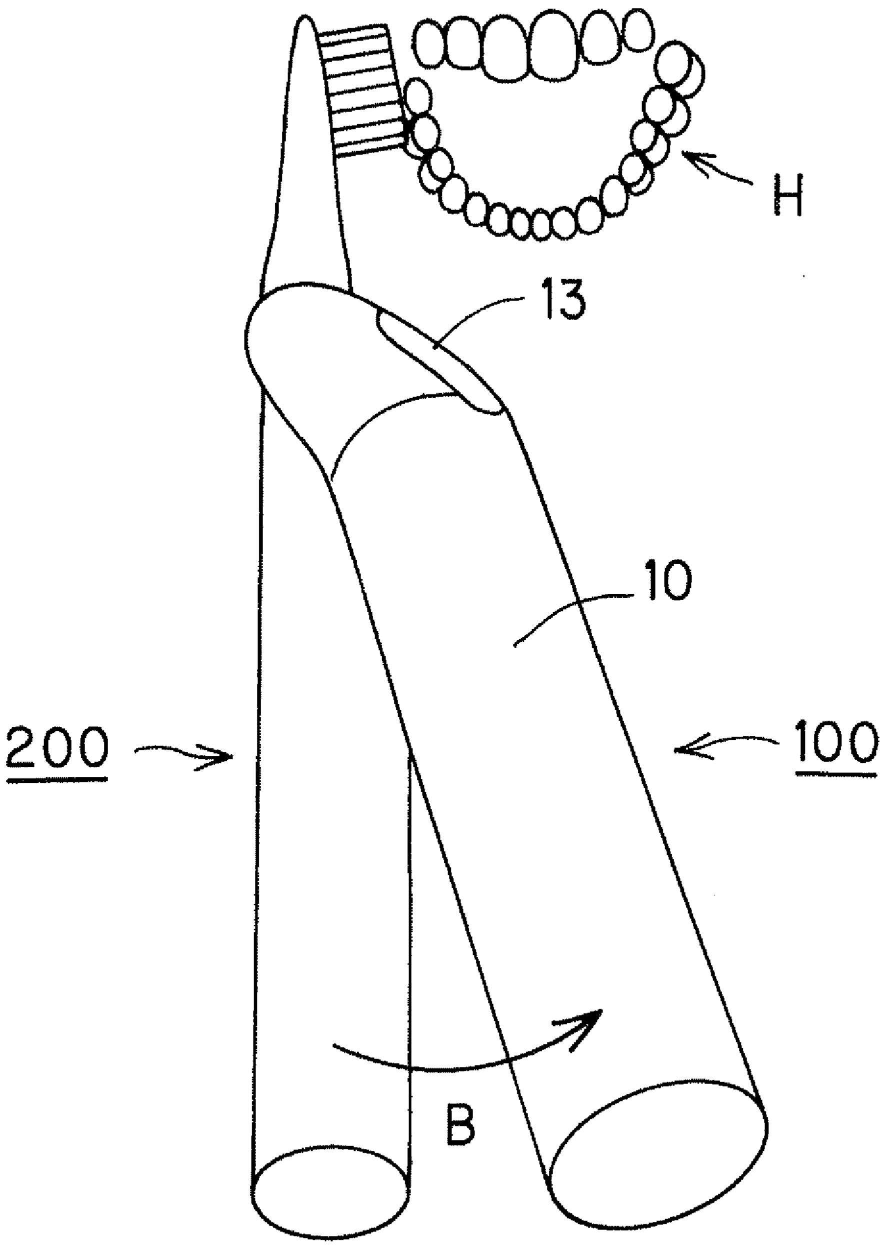
FIG. 7 is a view in which positions of the electric toothbrush according to the first embodiment of the present invention and the electric toothbrush according to the comparative example are compared to each other when the brush surface abuts (properly) on a right back tooth.

FIGS. 6 and 7 are views in which positions of the electric toothbrush according to the first embodiment of the present invention and an electric toothbrush according to a comparative example are compared to each other when a brush surface abuts (properly) on a back tooth (a left back tooth in FIG. 6 and a right back tooth in FIG. 7). An electric toothbrush 200 according to the comparative example is ordinarily configured such that the body portion and the intraoral insertion portion are aligned straight.

In FIGS. 6 and 7, symbol H designates a model of the teeth. As can be seen from FIGS. 6 and 7, when the brush surface abuts on the back tooth, in the electric toothbrush 100 according to the present embodiment, the body portion 11 is located inside (in the vicinity in front of the mouth) in comparison with the electric toothbrush 200 according to the comparative example (see an arrow A in FIG. 6 and an arrow B in FIG. 7).

Figure 8:
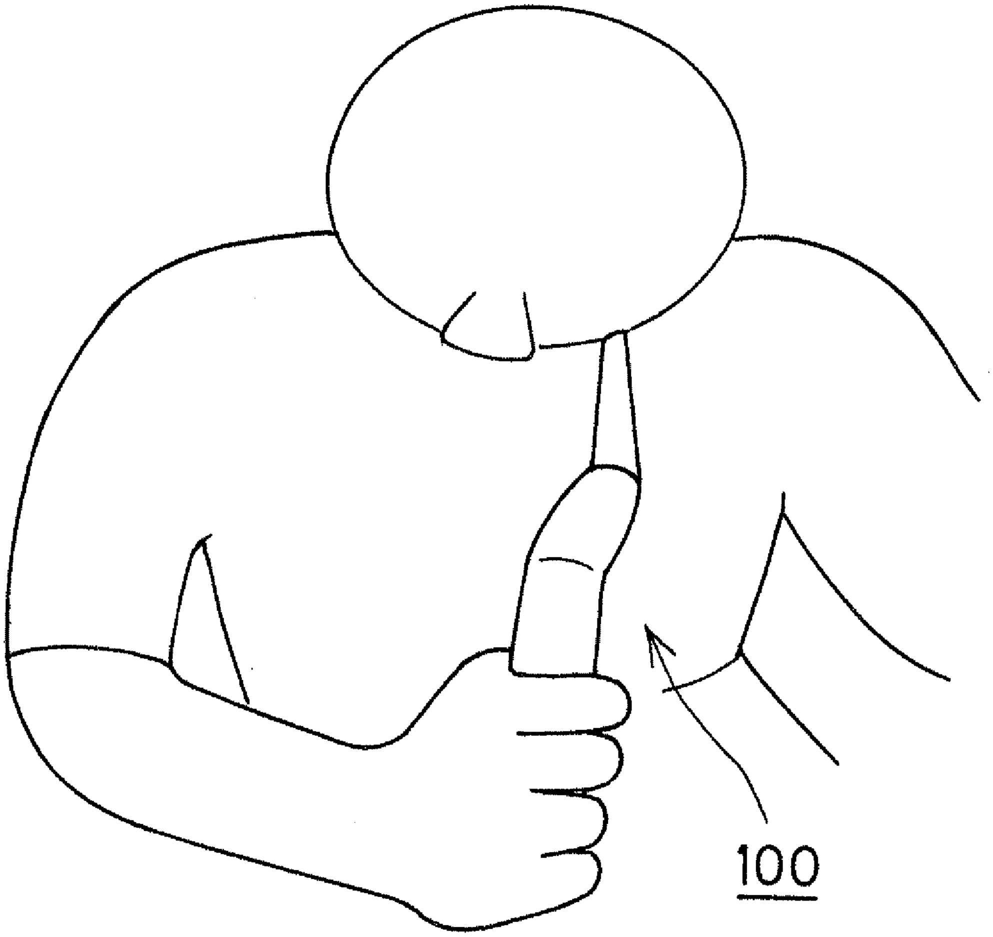
FIG. 8 is a schematic diagram illustrating a state in which toothbrushing is performed with the electric toothbrush according to the first embodiment of the present invention.
Figure 9:
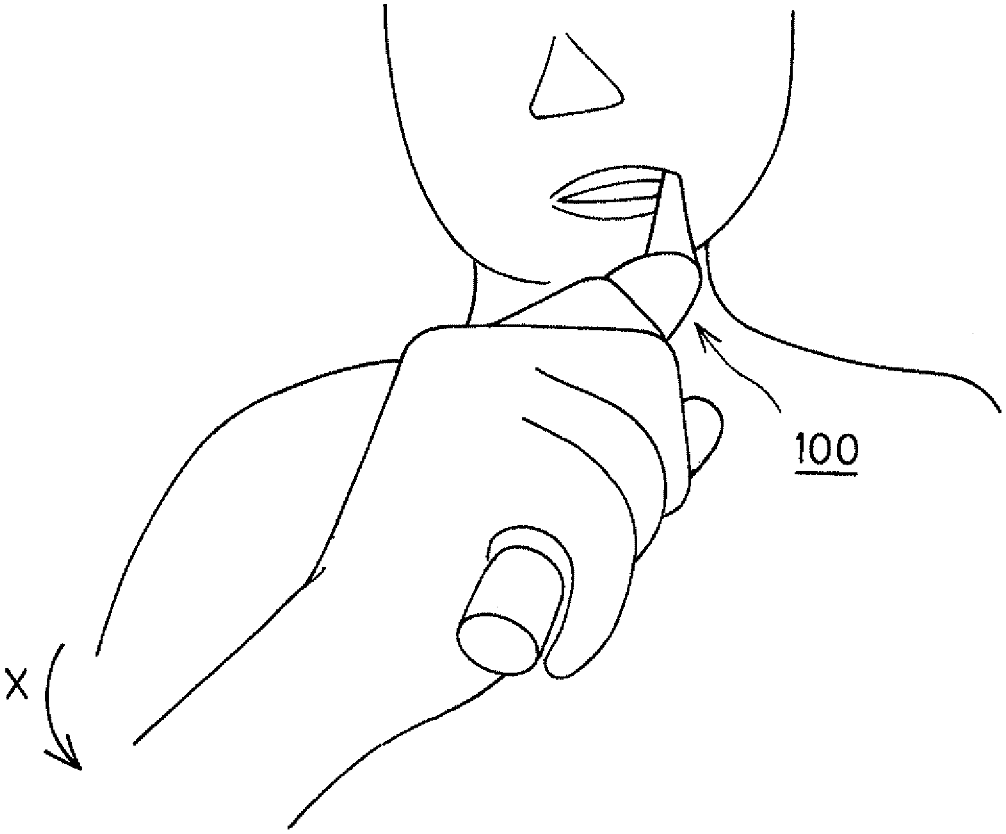
FIG. 9 is a schematic diagram illustrating a state in which toothbrushing is performed with the electric toothbrush according to the first embodiment of the present invention.
Figure 10:
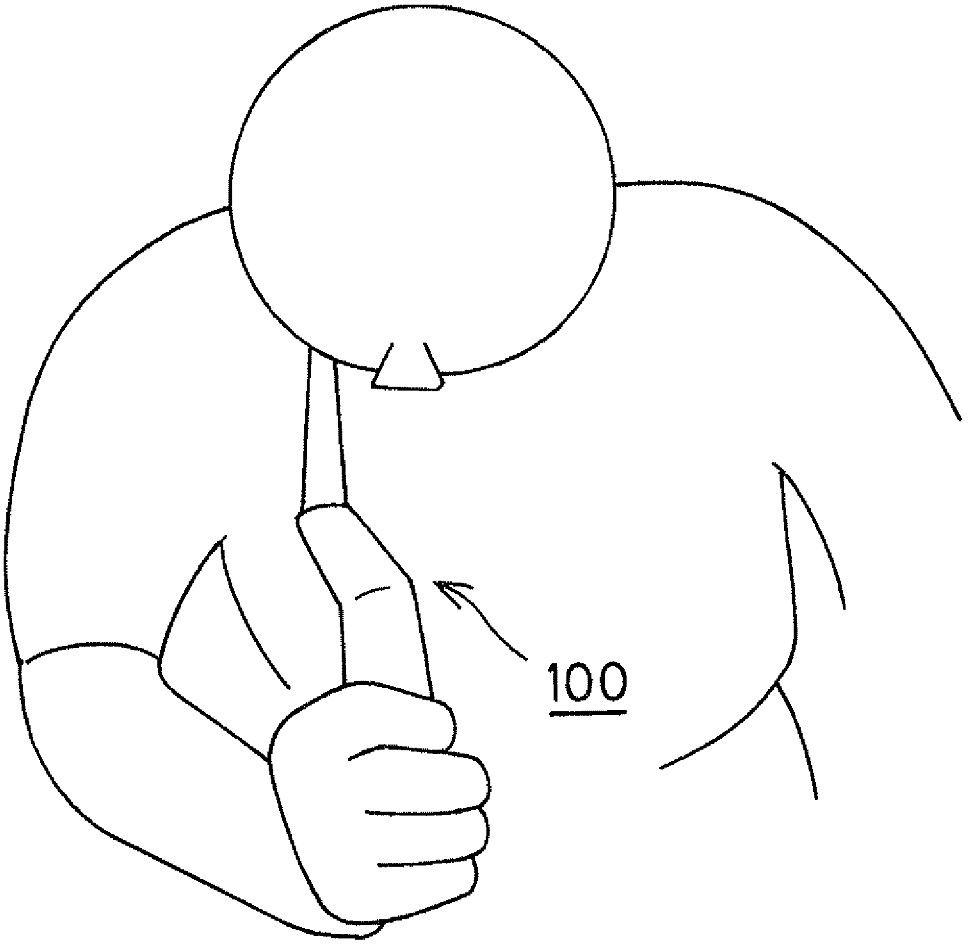
FIG. 10 is a schematic diagram illustrating a state in which toothbrushing is performed with the electric toothbrush according to the first embodiment of the present invention.
Figure 11:
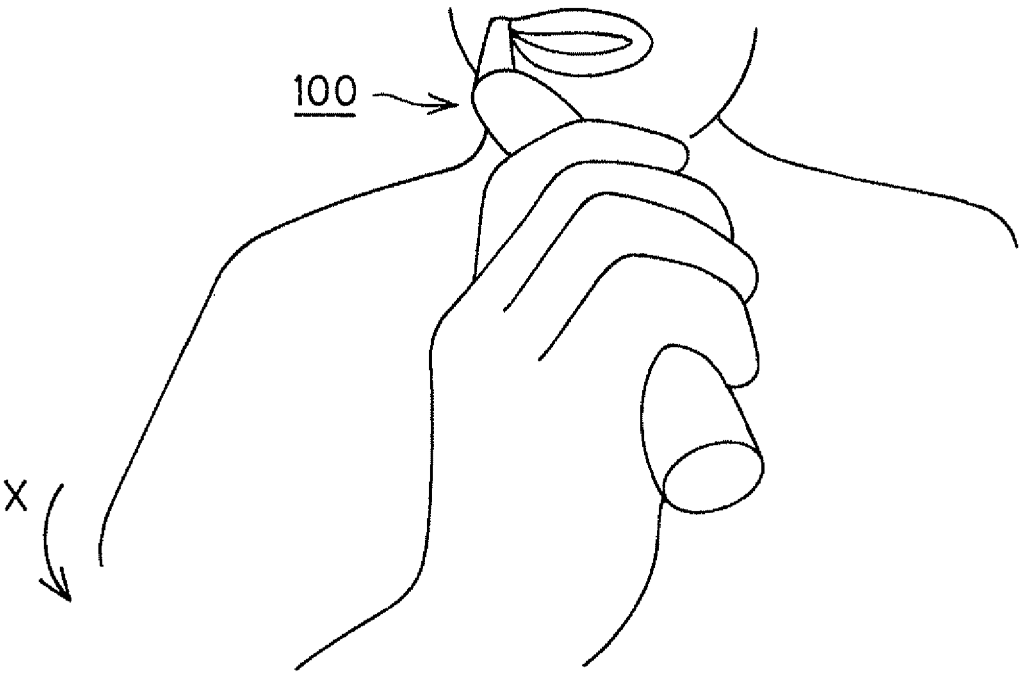
FIG. 11 is a schematic diagram illustrating a state in which toothbrushing is performed with the electric toothbrush according to the first embodiment of the present invention.

FIGS. 8 to 11 are schematic diagrams each illustrating a state in which toothbrushing is performed with the electric toothbrush according to the first embodiment of the present invention. Each of these figures illustrates a state in which the toothbrushing is performed while the electric toothbrush 100 is gripped by a right hand. FIG. 8 is a view illustrating a user brushing the left back tooth when viewed from obliquely above, and FIG. 9 is a view illustrating a user brushing the left back tooth when viewed from a front side, while FIG. 10 is a view illustrating a user brushing the right back tooth when viewed from obliquely above, and FIG. 11 is a view illustrating a user brushing the right back tooth when viewed from a front side.

As can be seen from these figures, when the toothbrushing is performed with the electric toothbrush 100 according to the first embodiment of the present invention, particularly when brushing the back tooth where imperfect brushing is easily caused, the toothbrushing can be performed in a relaxed pose without highly raising an elbow (particularly see an arrow X in FIGS. 9 and 11).

Figure 12:
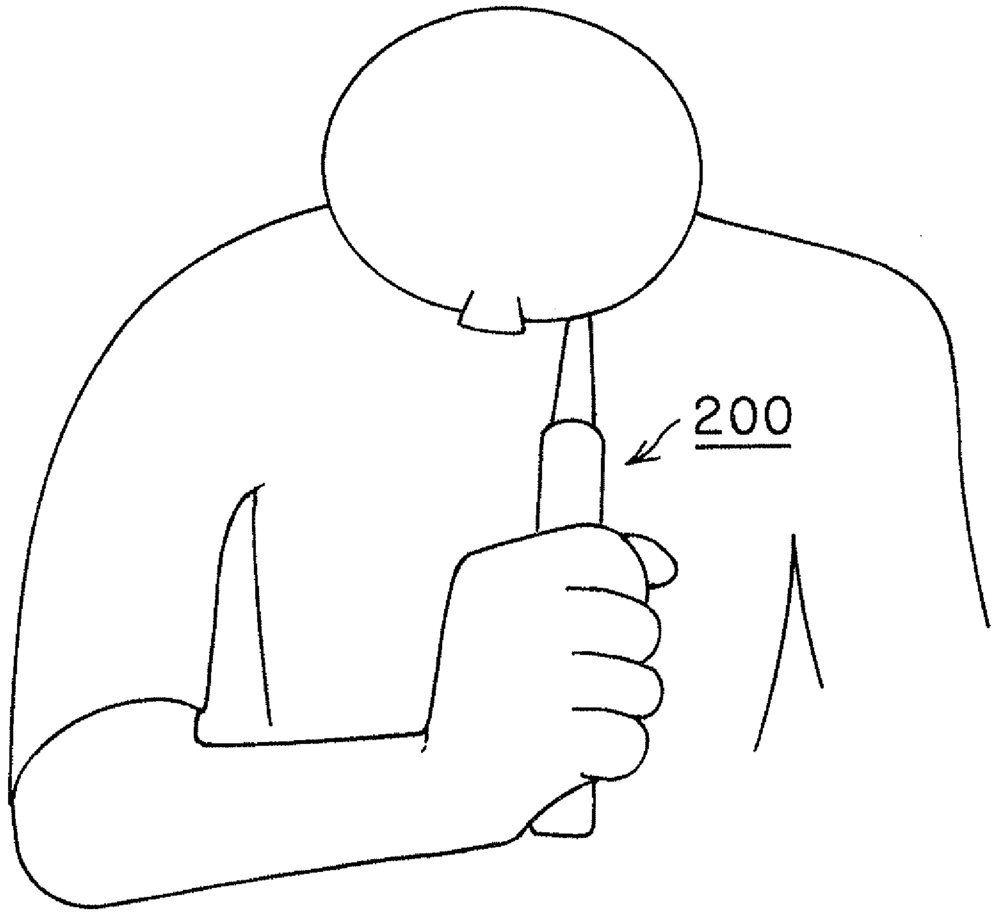
FIG. 12 is a schematic diagram illustrating a state in which toothbrushing is performed with the electric toothbrush according to the comparative example.
Figure 13:
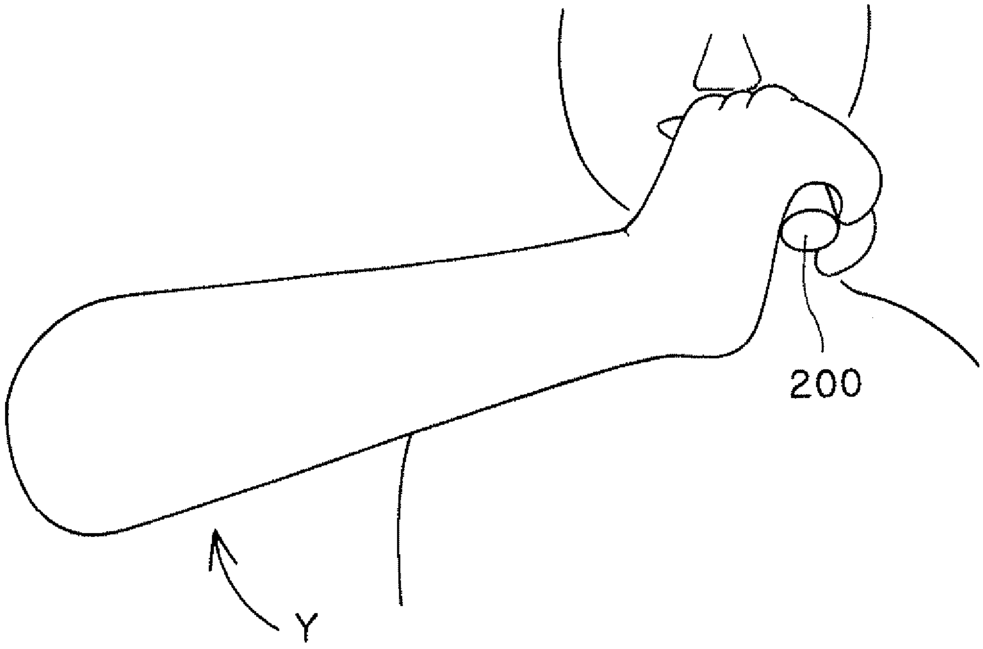
FIG. 13 is a schematic diagram illustrating a state in which toothbrushing is performed with the electric toothbrush according to the comparative example.
Figure 14:
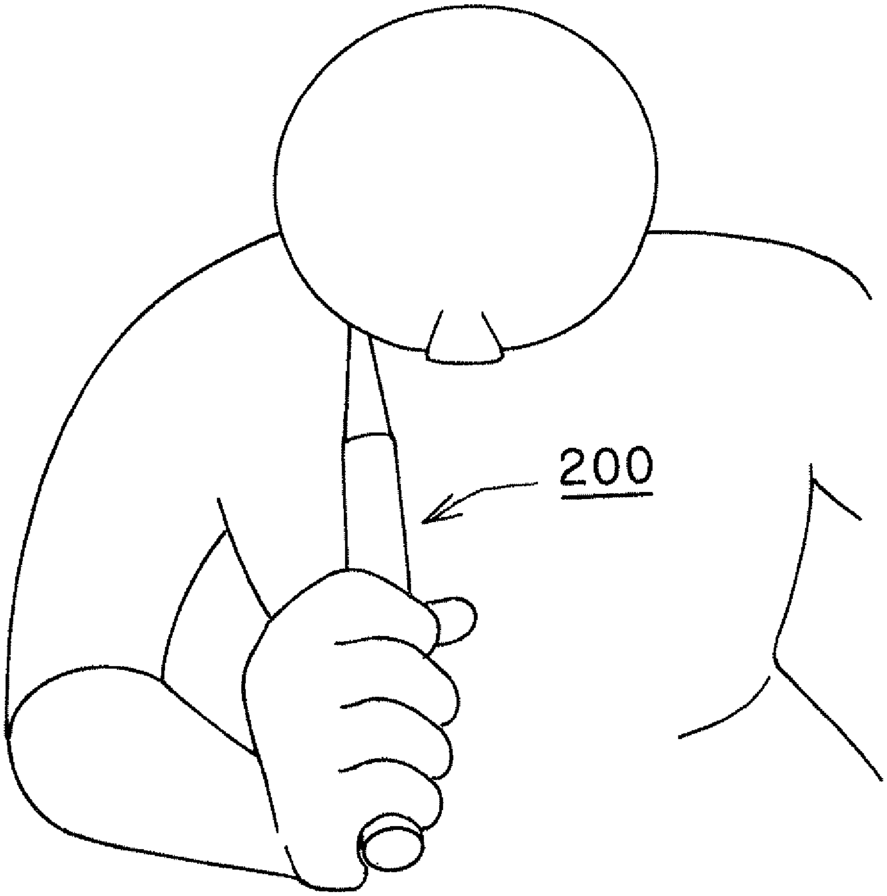
FIG. 14 is a schematic diagram illustrating a state in which toothbrushing is performed with the electric toothbrush according to the comparative example.

On the other hand, FIGS. 12 to 15 each illustrate a case where toothbrushing is performed with the electric toothbrush 200 according to the comparative example. FIGS. 12 to 15 are schematic diagrams each illustrating a state in which the toothbrushing is performed with the electric toothbrush according to the comparative example. Each of these figures illustrates a state in which the toothbrushing is performed while the electric toothbrush 200 is gripped by a right hand. FIG. 12 is a view illustrating a user brushing the left back tooth when viewed from obliquely above, FIG. 13 is a view illustrating a user brushing the left back tooth when viewed from a front side, while FIG. 14 is a view illustrating a user brushing the right back tooth when viewed from obliquely above, and FIG. 12 is a view illustrating a user brushing the right back tooth when viewed from a front side.

Figure 15:
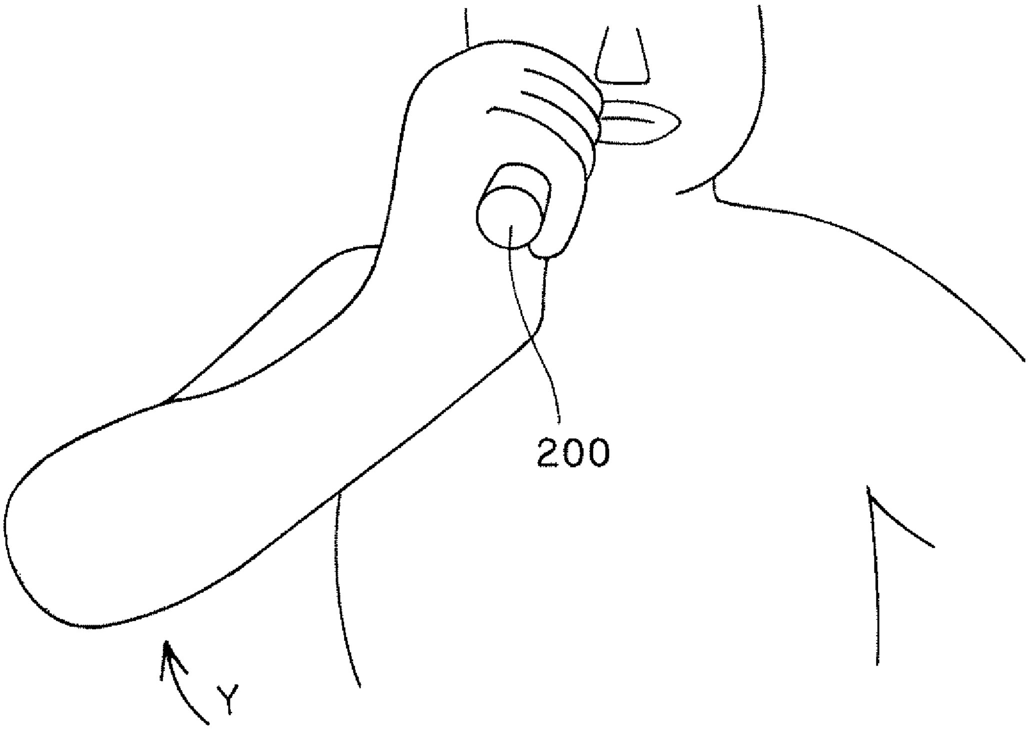
FIG. 15 is a schematic diagram illustrating a state in which toothbrushing is performed with the electric toothbrush according to the comparative example.

As can be seen from these figures, in the case where the toothbrushing is performed with the electric toothbrush 200 according to the comparative example, particularly when brushing the back tooth where imperfect brushing is easily caused, the toothbrushing is performed while the elbow is highly raised (particularly see an arrow Y in FIGS. 13 and 15). Accordingly, sometimes the user takes an unusual pose upon brushing the back tooth.

With the electric toothbrush 200 according to the comparative example, when the toothbrushing is performed while the electric toothbrush 200 is held at the position illustrated in each of FIGS. 6 and 7, there is caused no problem because the brush abuts properly on the back tooth. However, when the electric toothbrush 200 is held in the states illustrated in FIGS. 6 and 7, the user takes an unusual pose while the elbow is highly raised, as described above. Therefore, in actual the back tooth is possibly brushed while the electric toothbrush 200 is not held at the positions illustrated in FIGS. 6 and 7. That is, also in the case with the electric toothbrush 200 according to the comparative example, it is possible to have the brush abut on the back tooth such that the body portion of the electric toothbrush 200 is located inside (in the vicinity in front of the mouth). Even in such a case, the user obtains a feeling as if the brush abuts on the entire back tooth. However, in this case, the leading end surface of the brush is deviated from (is not parallel to) a plane in which the teeth are aligned. Accordingly, there may be a point where the leading end of the brush does not at all abut on the tooth, or the leading end of the brush is bent and an intermediate portion of the brush abuts on the tooth. Therefore caused is imperfect brushing.

On the other hand, in the case with the electric toothbrush 100 according to the present embodiment, when the brush 21 abuts on the back tooth in a relaxed and usual pose, the leading end surface of the brush is substantially parallel to the plane in which the teeth are aligned, and the brush can abut properly on the entire back tooth. Accordingly, imperfect brushing can be suppressed.

In the electric toothbrush 100 according to the present embodiment, while the brush 21 is vibrated by utilizing the eccentric shaft 35, the body portion 11 and the brush component 20 serving as the intraoral insertion portion are not aligned straight, as described above. That is, the electric toothbrush 100 according to the present embodiment is bent at two points between the body portion 11 and the connection portion 12 and between the connection portion 12 and the brush component 20 serving as the intraoral insertion portion. Adoption of such a configuration causes a negative factor from the viewpoint of a driving mechanism or transmission efficiency of the driving force.

However, in the electric toothbrush 100 according to the present first embodiment, the motor 32 serving as the driving source is provided in the connection portion 12. Therefore, only one bent point exists from the motor 32 serving as the driving source to the eccentric shaft 35. The flexible rod 37 is used only in a short section around the bent point.

The configuration described above can suppress the degradation of the transmission efficiency of the driving force from the rotating shaft of the motor 32 to the brush 21 in comparison with the ordinary electric toothbrush having the configuration in which the body portion and the intraoral insertion portion are aligned straight.

The motor 32 serving as the driving source is provided in the connection portion 12, so that the vibration of the motor 32 can be prevented from being transmitted to the body portion 11 that is griped by the hand. Accordingly, an uncomfortable feeling can be reduced during the toothbrushing.

In the electric toothbrush 100 according to the present embodiment, the display portion 13 is provided in the area including part of the surface on the side of the brush 21 of the connection portion 12.

Therefore, as can be seen from FIGS. 6 and 7, during the toothbrushing, the display portion 13 can be located opposite to the face of the user. Therefore, the user can recognize the display portion 13 even during the toothbrushing.

In the electric toothbrush 100 according to the present embodiment, the on-switch button 14*a* of the manipulation portion 14 is provided in the connection portion 12, and the off-switch button 14*b* is provided in the body portion 11. Accordingly, the user can easily distinguish these buttons from each other, and the user can simply perform the manipulation of powering on and off.

(Second Embodiment)

Figure 16:
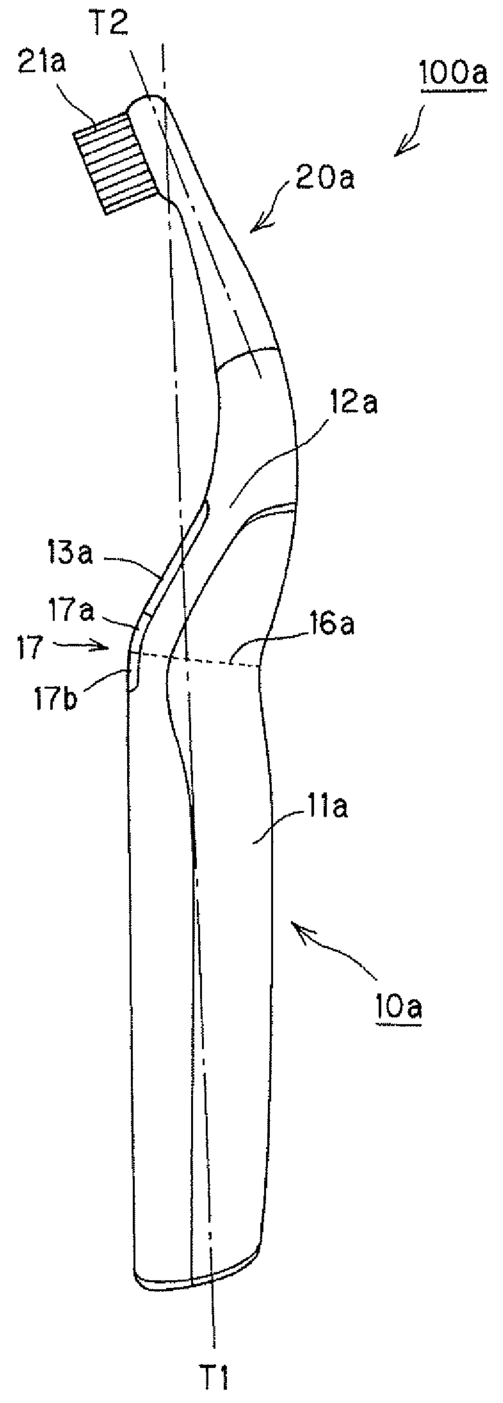
FIG. 16 is a side view of an electric toothbrush according to a second embodiment of the present invention.
Figure 17:
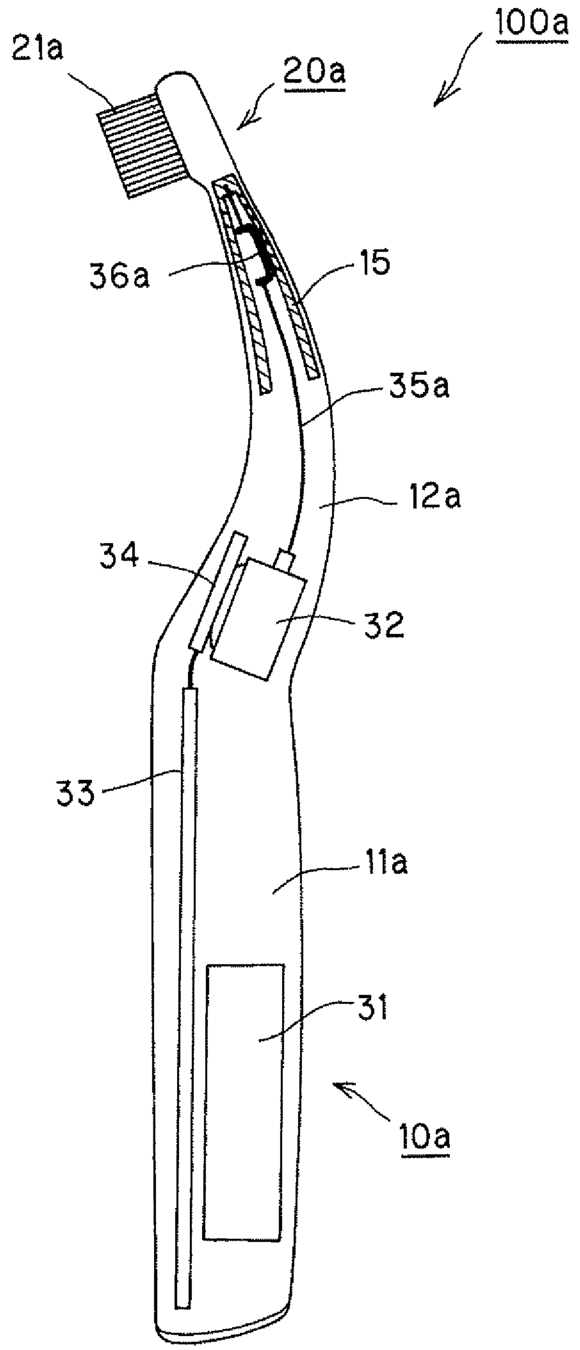
FIG. 17 is a schematic diagram (perspective view) illustrating a main configuration of an inside of the electric toothbrush according to the second embodiment of the present invention.

FIGS. 16 and 17 each illustrate a second embodiment of the present invention. In the present second embodiment, a connection portion that connects a body portion and an intraoral insertion portion (brush component) is curved, and an eccentric shaft itself has flexibility. Because other configurations and actions in the second embodiment are same as those according to the first embodiment, the same component is designated by the same symbol, and the description thereof is not provided where appropriate.

FIG. 16 is a side view of the electric toothbrush according to the second embodiment of the present invention. FIG. 17 is a schematic diagram (perspective view) illustrating a main configuration of an inside of the electric toothbrush according to the second embodiment of the present invention.

An electric toothbrush 100*a* according to the present embodiment includes a case 10*a* that includes a driving source therein and a brush component 20*a* that is detachably attached to the case 10*a*.

The brush component 20*a* is inserted in the mouth cavity during the toothbrushing, and the brush component 20*a* corresponds to the intraoral insertion portion. A brush 21*a* is provided at the leading end of the brush component 20*a*.

The case 10*a* according to the present embodiment includes a substantially cylindrical portion and a curved portion that is provided while being bent from a leading end portion 16*a* of the substantially cylindrical portion. The substantially cylindrical portion of the case 10*a* is gripped by the hand during the toothbrushing. Hereinafter, the substantially cylindrical portion gripped by the hand during the toothbrushing is referred to as a body portion 11*a*. The curved portion of the case 10*a* connects the body portion 11*a* and the brush component 20*a* serving as the intraoral insertion portion. Hereinafter, the curved portion is referred to as a connection portion 12*a*. A display portion 13*a* is provided in an area including part of a surface on the side of the brush 21*a* of the connection portion 12*a*. Also in the present embodiment, a manipulation portion 17 is provided adjacent to the display portion 13*a*. An on-switch button 17*a* is provided in the connection portion 12*a*, and an off-switch button 17*b* is provided in the body portion 11*a*.

In the electric toothbrush 100*a* according to the present embodiment, as described above, the body portion 11*a* is formed into the substantially cylindrical shape, and a virtual line connecting centroids of sectional shapes perpendicular to a longitudinal direction in the body portion 11*a* forms a substantially straight line. In FIG. 16, the alternate long and short dash line T1 includes the virtual line and an extended line of the virtual line. In the brush component 20*a* serving as the intraoral insertion portion, a portion except the brush 21*a* is formed into a substantially circular truncated cone shape. A virtual line connecting centroids of sectional shapes perpendicular to a longitudinal direction in this portion also forms a substantially straight line. In FIG. 16, the alternate long and short dash line T2 includes the virtual line and an extended line of the virtual line.

As can be seen from the relationship between the alternate long and short dash lines T1 and T2, the brush component 20*a* is inclined onto a rear surface side of the brush 21*a* from the leading end toward the body portion 11*a*. Also in the present embodiment, the brush component 20*a* is configured such that a back end of the brush component 20*a* is extended to a position projected toward the rear surface from the body portion 11*a*. The leading end portion of the brush component 20*a* is located in the vicinity of the extended line (alternate long and short dash line T1) of the virtual line that connects the centroids of the sectional shapes perpendicular to the longitudinal direction in the body portion 11*a*.

Although the present embodiment differs from the first embodiment regarding whether having a straight or bent shape, the connection portion 12*a* is inclined onto the rear surface side of the brush 21 from the leading end of the body portion 11*a* toward the brush 21*a*.

Also In the present embodiment, an eccentric shaft 35*a* including a weight 36*a* is provided on the leading end side of the case 10*a*, and a gravity center of the weight 36*a* is deviated from the axis center.

In the present embodiment, the eccentric shaft 35*a* itself has flexibility (that is, the eccentric shaft 35*a* is formed by a flexible rod). The rotating shaft of the motor 32 and the eccentric shaft 35*a* are directly coupled to each other.

Also in the case with the electric toothbrush 100*a* thus configured according to the present embodiment, there is obtained an effect similar to that of the electric toothbrush 100 according to the first embodiment. However, in the case with the electric toothbrush 100*a* according to the present embodiment, the eccentric shaft 35*a* itself has flexibility and the section in which the flexible rod is provided is longer than that of the first embodiment. Therefore, the transmission efficiency of the driving force is degraded in comparison with the first embodiment. However, the eccentric shaft 35*a* itself is formed by the flexible rod, which allows the number of component to be decreased in comparison with the first embodiment.

Description Of Symbols

10, 10*a* case
11, 11*a* body portion
12, 12*a* connection portion
13, 13*a* display portion
14 manipulation portion
14*a* on-switch button
14*b* off-switch button
15 stem
16, 16*a* leading end portion
17 manipulation portion
17*a* on-switch button
17*b* off-switch button
20, 20*a* brush component
21, 21*a* brush
31 battery
32 motor
33, 34 circuit board
35, 35*a* eccentric shaft
36, 36*a* weight
37 flexible rod
38 connection terminal
100, 100*a* electric toothbrush

The invention claimed is:

1. An electric toothbrush comprising:

a body portion that is gripped by a hand during toothbrushing;

an intraoral insertion portion that is inserted in a mouth cavity during the toothbrushing, the intraoral insertion portion including a brush at a leading end thereof and being inclined such that an axis of the intraoral insertion portion is inclined with respect to an axis of the body portion, and that an axis of the intraoral insertion portion intersects with the axis of the body portion at a location in a vicinity of the leading end portion of the intraoral insertion portion;

a connection portion located between the body portion and the intraoral insertion portion and being inclined such that one end of an axis of the connection portion intersects with the axis of the body portion and another end of the axis of the connection portion intersects with the axis of the intraoral insertion portion; and a display portion that is configured to display information regarding a brushing operation out of a plurality of brushing operations and is provided on the connection portion, the display portion being closer to the body portion than the intraoral insertion portion such that the display portion is viewable by a user during toothbrushing, wherein a surface of the display portion is inclined with respect to a surface of the body portion.

2. The electric toothbrush according to claim 1, further comprising a manipulation portion that includes a plurality of buttons to manipulate motions of the electric toothbrush is provided in an area from the body portion to the connection portion, wherein the buttons to perform different manipulations are disposed separately in the body portion and the connection portion.

3. The electric toothbrush according to claim 1, wherein the display portion is provided in an area including at least part of a surface on the brush side of the connection portion.

4. The electric toothbrush according to claim 1, wherein:

the axis of the intraoral insertion portion is a longitudinal axis through a center of the intraoral insertion portion, the axis of the body portion is a longitudinal axis through a center of the body portion and the axis of the connection portion is a longitudinal axis through a center of the connection portion, the axis of the intraoral insertion portion intersects with the axis of the body portion within the leading end portion of the intraoral insertion portion, the one end of the axis of the connection portion intersects with the axis of the body portion at an intersection of the body portion and the connection portion, and the another end of the axis of the connection portion intersects with the axis of the intraoral insertion portion within the connection portion.

5. The electric toothbrush according to claim 1, wherein the display portion is configured to separately display both information regarding the brushing operation out of the plurality of brushing operations and information regarding an elapsed period of time of the toothbrushing.

* * * * *